United States Patent [19]
Stanford et al.

[11] Patent Number: 5,833,996
[45] Date of Patent: Nov. 10, 1998

[54] **TREATMENT OF PSORIASIS USING DEAD CELLS OF *MYCOBACTERIUM VACCAE***

[75] Inventors: John Lawson Stanford, Marden; Graham Arthur William Rook, Haver Hill, both of United Kingdom

[73] Assignee: University College London, London, England

[21] Appl. No.: 441,980

[22] Filed: May 16, 1995

Related U.S. Application Data

[63] Continuation of Ser. No. 238,795, May 6, 1994, abandoned, which is a continuation of Ser. No. 835,948, filed as PCT/GB90/01318 Aug. 24, 1990 published as WO91/02542 Mar. 7, 1991, abandoned.

[30] Foreign Application Priority Data

Aug. 25, 1989 [GB] United Kingdom ............... 8919321

[51] Int. Cl.$^6$ .................................................. A61K 39/04
[52] U.S. Cl. ..................... 424/248.1; 424/278.1; 424/93.4; 530/350; 530/395
[58] Field of Search ............... 424/184.1, 248.1, 424/282.1, 278.1, 93.4; 435/69.3; 514/2, 8; 530/395, 868, 350

[56] References Cited

U.S. PATENT DOCUMENTS

| | | | |
|---|---|---|---|
| 4,404,194 | 9/1983 | Arala-Chaves | 424/177 |
| 4,716,038 | 12/1987 | Stanford et al. | 424/248.1 |
| 4,724,144 | 2/1988 | Rook et al. | 424/248.1 |
| 5,114,844 | 5/1992 | Cohen et al. | 435/7.21 |
| 5,599,545 | 2/1997 | Stanford et al. | 424/282.1 |

FOREIGN PATENT DOCUMENTS

| | | | |
|---|---|---|---|
| 0 262 710 | 4/1988 | European Pat. Off. | A61K 37/02 |
| 0 322 990 | 7/1989 | European Pat. Off. | C07K 7/06 |
| WO 85/05034 | 11/1985 | WIPO | A61K 35/74 |

OTHER PUBLICATIONS

Kim, M.S. et al., EMBASE abstract 76115069 of Korean J. Dermatol. 13(1):25–31, "Therapeutic trial of BCG in patients with psoriasis", 1975.

Braude, et al. *Infections Disease and Medical Microbiology* (2nd ed.) (1986), pp. 364–371.

Coltran, et al. *Robbins Pathelogical Basis of Disease*, (1989), 4th edition, pp. 1299–1301.

Fillex, E, et al., Clin. Exp. Immunol., 76; 343–347 (Jun. 1989), "A transient n5e in agalactosyl lgG correlating with Free tL–2 receptors . . ."

Parekh, R. B. et al. Nature 316:452–457 (1985), "Association of rheumatoid arthritis and primary osteo–arthritis with changes in the glycosylation pattern of total serum lgG".

Wand–Würftenberger A et al. Eur. J. Immunol. 21:1089–1092 (1991), "Surface expression by mononuclear Phagocytes of an epitope shared with mycobacterial hsp 65.".

Racemacher, T.W. et al. Springer Semin. Immunopathology 10:231–49 (1988) "Role of IgG Glycoforms in the Pathogenesis of Rheumatoid Arthritis."

*Primary Examiner*—Thomas M. Cunningham
*Attorney, Agent, or Firm*—Armstrong, Westerman, Hattori, McLeland & Naughton

[57] ABSTRACT

Immunoregulatory material derived from *Mycobacterium vaccae*, especially dead cells of *M. vaccae*, are useful for the treatment of pathological conditions (other than mycobacterial disease and arthritic disease) in a patient in which the patient's IgG shows an abnormally high proportion of agalactosyl IgG and for the treatment of chronic inflammatory disorders (other than an arthritic disease) caused or accompanied by an abnormally high release from macrophages of interleukin-6 and/or tumor necrosis factor.

3 Claims, No Drawings

TREATMENT OF PSORIASIS USING DEAD CELLS OF *MYCOBACTERIUM VACCAE*

This application is a continuation of application Ser. No. 08/238,795 filed May 6, 1994, now abandoned, which was the continuation of application Ser. No. 07/835,948, filed Apr. 13, 1992, abandoned, which was a national stage under §371 of application PCT/GB90/01318 filed Aug. 24, 1990 published as WO91/02542 Mar. 7, 1991.

This invention relates to the treatment of chronic inflammatory conditions, e.g. psoriasis.

British Specification No. 2156673 (International Patent Specification W085/03639) describes immunotherapeutic agents comprising killed cells of *Mycobacterium vaccae*. These agents are useful in the immunotherapy of mycobacterial disease, especially tuberculosis and leprosy. It is stated that use of this immunotherapeutic agent facilitates the removal of the persisting bacilli responsible for tuberculosis or leprosy which, as is well known, it is difficult to remove by chemotherapy alone. It is suggested in the specification that the immunotherapeutic agent is believed to act by presenting the "protective" common mycobacterial antigens to advantage and by containing immune suppressor determinants which are active in regulating disadvantageous immune mechanisms. As a consequence, "persister" bacilli are recognized by the immune system by their content of common mycobacterial antigens and effective immune mechanisms are directed against them, in the absence of the tissue necrotic form of immunity usually present in mycobacterial disease.

International Patent Specification PCT/GB85/00183 (W085/05034) describes compositions for the alleviation of the symptoms of, and for the treatment or diagnosis of, arthritic disease which comprise as active ingredient the whole organism of *M. vaccae*. It is stated that the preparations of *M. vaccae* are useful for the treatment of various autoimmune diseases and especially arthritic conditions including rheumatoid arthritis, ankylosing spondylitis or Reiter's syndrome.

We have now discovered that compositions comprising antigenic and immunoregulatory material derived from *Mycobacterium vaccae* are generally useful in the treatment of pathological conditions in which the proportion of agalactosyl IgG (i.e. IgG which lacks terminal galactose from the N-linked oligosaccharides on the heavy chains) is increased. Diseases of this kind include not only the arthritic disease e.g. rheumatoid arthritis, and mycobacterial disease, e.g. tuberculosis and leprosy, mentioned in the specifications referred to above, but also Crohn's disease. Other diseases in which this may play a part but in which an increased level of agalactosyl IgG is not easily detectable by current methods include primary biliary cirrhosis, sarcoidosis, ulcerative colitis, psoriasis, systemic lupus erythematosus (especially when accompanied by Sjogren's syndrome), multiple sclerosis, Guillain-Barré syndrome, primary diabetes mellitus, and perhaps some aspects of graft rejection.

Such diseases may also be described as that class of chronic inflammatory disorder which is caused by, or accompanied by, abnormally high release by macrophages of the cytokines interleukin-6 and/or tumour necrosis factor (cachectin). The specific conditions involved are, of course, the same as those already named.

The present invention accordingly provides a method for the treatment of a pathological condition (other than mycobacterial disease, e.g. tuberculosis or leprosy, and arthritic disease, e.g. rheumatoid arthritis, mentioned in the specifications referred to above) in a patient in which the patient's IgG shows an abnormally high proportion of agalactosyl IgG which comprises administering to the patient suffering from such a condition an effective amount of a therapeutic composition comprising antigenic and immunoregulatory material derived from *Mycobacterium vaccae*.

The invention also provides a method for the treatment of a chronic inflammatory disorder (other than an arthritic disease, e.g. rheumatoid arthritis) caused or accompanied by an abnormally high release from macrophages of interleukin-6 and/or tumour necrosis factor which comprises administering to a patient suffering from such a disorder an effective amount of the said therapeutic agent.

The invention further provides antigenic and immunoregulatory material derived from *M. vaccae* for use in the manufacture of a therapeutic agent for the treatment of pathological conditions (other than mycobacterial disease or arthritic disease) in a patient whose IgG shows an abnormally high proportion of agalactosyl IgG. Such antigenic and immunoregulatory material is also provided for use in the manufacture of a therapeutic agent for use in the treatment of a chronic inflammatory disorder (other than arthritic disease) of the kind mentioned above.

The therapeutic agent of the invention conveniently, and therefore preferably, comprises dead cells of *M. vaccae*, most preferably cells which have been killed by autoclaving or by irradiation. The therapeutic agent normally comprises more than $10^8$ to $10^{11}$ killed *M. vaccae* microorganisms per ml of diluent.

The diluent may be pyrogen-free saline for injection alone, or a borate buffer of pH 8.0. The diluent should be sterile. A suitable borate buffer is:

| | |
|---|---|
| $Na_2B_4O_7 \cdot 10H_2O$ | 3.63 g |
| $H_3BO_3$ | 5.25 g |
| NaCl | 6.19 g |
| Tween 80 | 0.0005% |
| Distilled Water | to 1 litre |

The preferred strain of *M. vaccae* is one denoted R877R isolated from mud samples from the Lango district of Central Uganda (J. L. Stanford and R. C. Paul, Ann. Soc. Belge Med, Trop. 1973, 53 141–389). The strain is a stable rough variant and belongs to the aurum sub-species. It can be identified as belonging to *M. vaccae* by biochemical and antigenic criteria (R. Bonicke, S. E. Juhasz., Zentr albl. Bakteriol. Parasitenkd. Infection skr. Hyg. Abt. 1, Orig., 1964, 192, 133).

The strain denoted R877R has been deposited under the Budapest Convention at the National Collection of Type Cultures (NCTC) Central Public Health Laboratory, Colindale Avenue, London NW9 5HT, United Kingdom on Feb. 13th, 1984 under the number NCTC 11659.

For the preparation of the therapeutic agent, the microorganism *M. vaccae* may be grown on a suitable solid medium. A modified Sauton's liquid medium is preferred (S. V. Boyden and E. Sorkin., J. Immunol, 1955 75, 15) solidified with agar. Preferably the solid medium contains 1.3% agar. The medium inoculated with the microorganisms is incubated aerobically to enable growth of the microorganisms to take place, generally at 32° C. for 10 days. The organisms are harvested, then weighed and suspended in a diluent. The diluent may be unbuffered saline but is preferably borate-buffered and contains a surfactant such as Tween 80 as described above. The suspension is diluted to give 100 mg of microorganism/ml. Fur further dilution, borate buffered saline is preferably used so that the suspension contains 10 mg wet weight of microorganisms/ml of diluent. The suspension may then be dispensed into 5 ml multidose vials. Although the microorganisms in the vials may be killed using irradiation e.g. from $^{60}$Cobalt at a dose of 2.5 megarads, or by any other means, for example chemically, it is preferred to kill the microorganisms by autoclaving, for example at 10 psi (69 kPa) for 10 minutes (115°–125° C.). It has been discovered, unexpectedly, that autoclaving yields a more effective preparation than irradiation.

The therapeutic agent is in general administered by injection in a volume in the range 0.1–0.2 ml, preferably 0.1 ml, given intradermally. A single dosage will generally contain from $10^7$ to $10^{10}$ killed *M. vaccae* microorganisms. It is preferred to administer to patients a single dose containing $10^8$ to $10^9$ killed *M. vaccae*. However, the dose may be repeated depending on the condition of the patient.

While the present invention does not depend on the truth of this theory it is believed that the active ingredient in the killed *M. vaccae* may be the 65 kDa mycobacterial heat shock protein (hsp 65) described by Young et al. "Stress proteins are immune targets in leprosy and tuberculosis", Proc. Natl. Acad. Sci. U.S.A. 85 (1988), pp4267–4270 in a form obtained from *M. bovis*. The preferred autoclaved *M. vaccae* cells used in the present invention are believed to provide an effective package of the hsp 65 and other substances in a convenient adjuvant.

Although the therapeutic agent will generally be administered by intradermal injection, other routes, e.g. oral administration, can also be used.

It may be advantageous and is within the scope of the invention to use more than one strain of *M. vaccae*, and/or to include in the immunoprophylactic agent other mycobacterial antigens. Tuberculin may also be included.

The immunoprophylactic agent may also contain BCG (Bacillus Calmette-Guerin) vaccine, in particular the freeze-fried form of the vaccine, to promote its effect.

The therapeutic agent can contain further ingredients such as adjuvants, preservatives, stabilisers etc. It may be supplied in sterile injectable liquid form or in sterile freeze-fried form which is reconstituted prior to use.

*M. vaccae* may be used as such or as an extract or fractioned portion of the organism to manufacture the therapeutic agents according to the invention.

The following Example illustrates the invention.

EXAMPLE

*M. vaccae* NCTC 11659 is grown on a solid medium comprising modified Sauton's medium solidified with 1.3% agar. The medium is inoculated with the microorganism and incubated for 10 days at 32° C. to enable growth of the microorganism to take place. The microorganisms are then harvested by gently scraping the surface of the agar and weighed (without drying) and suspended in M/15 borate buffered saline at pH8 to give 10 mg of microorganisms/ml of saline. The suspension is dispensed into 5 ml vials, and then autoclaved for 10 minutes at 10 psi (69 kPa) to kill the microorganisms. After cooling, 1/10th volume of tuberculin (at the standard concentration of 2 µg/ml) is added. The therapeutic agent thus produced is stored at 44° C. before use. A single dose consists of 0.1 ml of the suspension, which should be shaken vigorously immediately before use, containing 1 mg wet weight of *M. vaccae* and 0.02 µg of tuberculin. The dose is given by intradermal injection normally over the left deltoid muscle.

Only one dose is normally required. The patient should not receive high dose steroids or other immuno-suppressive therapy. Up to six months may elapse before the beneficial effect becomes apparent.

We claim:

1. A method for the treatment of psoriasis in a patient comprising administering to the patient in need of such treatment an amount effective to alleviate said psoriasis of an immunoregulatory material derived from *Mycobacterium vaccae*, said material comprising dead cells of *Mycobacterium vaccae*.

2. A method according to claim 1, wherein the material derived from *M. vaccae* comprises cells of *M. vaccae* that have been killed by autoclaving.

3. A method according to claim 1, wherein the material derived from *M. vaccae* is derived from the strain as deposited at the National Collection of Type Cultures (NCTC) Central Public Health Laboratory, Colindale Avenue, London NH9 5HT, United Kingdom on Feb. 13th, 1984 under the number NCTC 11659.

* * * * *